(12) United States Patent
Maruyama

(10) Patent No.: US 8,354,393 B2
(45) Date of Patent: Jan. 15, 2013

(54) FILM PREPARATION AND PROCESS FOR PREPARING THE SAME

(75) Inventor: Naosuke Maruyama, Joetsu (JP)

(73) Assignee: Shin-Etsu Chemical Co., Ltd., Chiyoda-ku, Tokyo (JP)

( * ) Notice: Subject to any disclaimer, the term of this patent is extended or adjusted under 35 U.S.C. 154(b) by 0 days.

(21) Appl. No.: 13/155,963

(22) Filed: Jun. 8, 2011

(65) Prior Publication Data

US 2011/0236562 A1    Sep. 29, 2011

Related U.S. Application Data

(62) Division of application No. 11/117,260, filed on Apr. 28, 2005, now Pat. No. 7,976,864.

(30) Foreign Application Priority Data

Apr. 28, 2004  (JP) ................................. 2004-132644

(51) Int. Cl.
*A61K 31/715* (2006.01)

(52) U.S. Cl. ........................................................ 514/57

(58) Field of Classification Search ........................ None
See application file for complete search history.

(56) References Cited

U.S. PATENT DOCUMENTS

| | | | |
|---|---|---|---|
| 4,076,935 A * | 2/1978 | Eichenseer et al. | 536/86 |
| 4,091,205 A | 5/1978 | Onda et al. | |
| 4,126,502 A | 11/1978 | Dabal et al. | |
| 4,695,465 A | 9/1987 | Kigasawa et al. | |
| 4,713,243 A * | 12/1987 | Schiraldi et al. | 424/676 |
| 4,900,554 A | 2/1990 | Yanagibashi et al. | |
| 5,914,118 A | 6/1999 | Yamamura et al. | |
| 6,042,844 A | 3/2000 | Ishida et al. | |
| 6,849,729 B2 | 2/2005 | Obara | |
| 6,939,559 B1 | 9/2005 | Nishibe et al. | |
| 2003/0008019 A1 | 1/2003 | Nishibe et al. | |
| 2003/0166918 A1 | 9/2003 | Obara | |
| 2004/0126330 A1 | 7/2004 | Awamura et al. | |
| 2005/0136084 A1 | 6/2005 | Fukasawa et al. | |
| 2005/0142186 A1 | 6/2005 | Hayakawa et al. | |
| 2005/0181054 A1 | 8/2005 | Nishibe et al. | |

FOREIGN PATENT DOCUMENTS

| | | |
|---|---|---|
| EP | 1120427 A1 * | 8/2001 |
| EP | 1 543 828 A1 | 6/2005 |
| GB | 1108837 | 3/1968 |
| JP | 55-071537 | 5/1980 |
| JP | 57-53100 | 11/1982 |
| JP | 6-48917 | 2/1994 |
| JP | 7-82171 | 3/1995 |
| JP | 9-235220 | 9/1997 |
| JP | 9-238738 | 9/1997 |
| JP | 10-158302 | 6/1998 |
| JP | 2001-502678 | 2/2001 |
| JP | 2002-204951 | 7/2002 |
| JP | 2003-95947 | 4/2003 |
| JP | 2003-300852 | 10/2003 |

OTHER PUBLICATIONS

European Search Report for European Application No. 05 25 2581 dated Aug. 1, 2005.

* cited by examiner

*Primary Examiner* — Anand Desai
*Assistant Examiner* — Melissa Mercier
(74) *Attorney, Agent, or Firm* — Alston & Bird LLP

(57) ABSTRACT

An object is to provide a film preparation comprising a polymer harmless to living bodies and being highly adhesive to the skin; and a film preparation further containing a pharmaceutically active oily ingredient and being highly adhesive to the skin. More specifically, provided is a film preparation comprising a drug, a wetly shear-triturated low-substituted cellulose ether having a molar substitution of from 0.05 to 1.0 per anhydrous glucose unit, and a water-soluble cellulose ether, and having 100 minutes or greater of adhesion ability to the skin. The preparation becomes a skin-adhesive hydrous sheet having excellent skin adhesion after it is wet with water as it is used.

5 Claims, No Drawings

FILM PREPARATION AND PROCESS FOR PREPARING THE SAME

CROSS-REFERENCE TO RELATED APPLICATIONS

This application is a divisional of U.S. application Ser. No. 11/117,260, filed Apr. 28, 2005, now U.S. Pat. No. 7,976,864 which claims priority to Japanese Application No. 2004-132644, filed Apr. 28, 2004, each of which is incorporated herein by reference in their entirety.

BACKGROUND OF THE INVENTION

1. Field of the Invention

The present invention relates to a gel sheet used for cosmetics, pharmaceuticals and the other applications, particularly to a cosmetic sheet or percutaneous absorption preparation to be applied to the skin.

2. Description of the Related Art

Gel sheets mainly comprising agar or the like are conventionally known. Since the agar as a gel forming component forms a network structure in water, such gel sheets can be used for the purpose of moisture retention. The gel sheets made of agar however do not have a sufficient strength and in addition, there is a difficulty in incorporating an oily pharmaceutically active ingredient therein.

Gel sheets using an acrylic polymer gel are, on the other hand, not free from the fear of toxicity of the residual monomer and those with less irritation to the skin are requested. Many gel sheets need a crosslinking agent, the use of which complicates their preparation process. It is also impossible to incorporate a pharmaceutically active oily ingredient in such gels freely.

Many of cosmetic sheets to be applied to the skin such as face or hands contain therein a moisturizing agent and a polymer for supporting the moisturizing agent therewith, or are used after applying components containing a moisturizing agent to the sheet. For example, a cosmetic moisturizing sheet containing a moisturizing agent such as hyaluronic acid or collagen supported on a fiber sheet is disclosed in Japanese Patent Application Unexamined Publication No. 9-238738/1997. A cosmetic pack comprising chitosan and a medium paste, and a collagen-free moisturizing mask obtained by crosslinking a cationic biopolymer are disclosed in Japanese Patent Unexamined Application Nos. 6-48917/1994 and 2001-502678, respectively.

The above-described gel sheet is typically a paper sheet impregnated with a moisturizing agent. It does not have a sufficient water retention capacity and in addition, the paper sheet causes a sense of discomfort upon use. Gel polymers have improved adhesion to the skin, but are not sufficient. Another drawback of them is a complicated preparation process owing to the use of a crosslinking agent.

As a countermeasure against the above-described problems, a gel sheet of cellulose ether having a low molar substitution is disclosed in Japanese Patent Application Unexamined Publication No. 6-48197/1994. The gel sheet is free from the problem of a monomer which occurs upon use of an acrylic polymer, can be prepared without extra effort because a crosslinking agent is not necessary. The gel sheet has a sufficient water retaining capacity, and does not cause any sense of discomfort upon use. When such a sheet is applied to the body, however, it peels off the body before a drug such as a moisturizing agent, an anti-wrinkle agent, an anti-spot agent or a whitening cosmetic with which the sheet has been impregnated starts exhibition of its effect (about 20 minutes). It cannot keep its adhesion for at least 60 minutes, time at least necessary for the effective delivery of the chemical substance. Thus, the gel sheet has a drawback in skin adhesion. The above-described hydrous sheet of low-substituted cellulose ether can be prepared by casting an alkaline solution of low-substituted cellulose ether onto a supporting plate, neutralizing and coagulating the sheet with an acid and then washing off, from the sheet, the salt formed by neutralization. In order to produce a sheet containing a pharmaceutically active ingredient, the pharmaceutically active ingredient is added in advance upon preparation of an alkaline solution, or a sheet formed is dipped in a solution containing the pharmaceutically active ingredient. However, depending on a type of pharmaceutically active ingredient, production of sheet containing the pharmaceutically active ingredient has problems, for example, that the ingredient is decomposed in the alkaline solution, it does not dissolve in the solution smoothly, or a sufficient amount of the ingredient cannot be supported in the sheet even if the sheet is dipped in an aqueous solution of the ingredient. Moreover, an oily substance immiscible with water cannot be incorporated.

There is a process of preparing a hydrous gel sheet having improved skin adhesion, which comprises casting, on a supporting plate, a mixture of an alkaline solution of low-substituted cellulose ether and water-soluble and alkali-soluble cellulose ether having a substitution degree of 1.1 to 1.4, neutralizing and coagulating a sheet of the mixture on the plate with an acid, and washing off the salt in the sheet. By this process, however, it is impossible to prepare a hydrous sheet having a high content of water-soluble cellulose ether because a portion of the water-soluble cellulose ether leaks out during the washing step for removing the neutralization salt, leading to a reduction in the strength of the hydrous sheet. The higher the content of the water-soluble cellulose ether is, the better the skin adhesion of the sheet is. The sheet obtained by the above-described method therefore does not have sufficient skin adhesion.

As percutaneous absorption preparations, a nicotine-containing film preparation is disclosed in Japanese Patent Application Unexamined Publication No. 2003-95947. A skin adhesive film preparation obtained by incorporating a water-soluble cellulose lower-alkyl ether in a fibroblast growth factor is disclosed in Japanese Patent Application Unexamined Publication No. 7-82171/1995. A membrane-attached adhesive multilayer film preparation comprising a water-soluble polymer layer containing a drug and an adhesive layer containing an adhesive substance is disclosed in Japanese Patent Application Unexamined Publication No. 9-235220/1997. Any of them does not relate to a hydrous sheet containing low-substituted cellulose ether.

SUMMARY OF THE INVENTION

With the foregoing in view, the present invention has been completed. An object of the present invention is to provide a hydrous gel sheet comprising a polymer harmless to the living body and being highly adhesive to the skin. Another object of the invention is to provide a hydrous gel sheet comprising a pharmaceutically-active oily ingredient and being highly adhesive to the skin.

The present inventors have carried out an extensive investigation with a view to attaining the above-described objects. As a result, it has been found that a film preparation containing a desired amount of drug can be prepared by casting a mixture onto a supporting plate wherein the mixture comprises a drug, wetly shear-triturated low-substituted cellulose ether having a molar substitution of 0.05 to 1.0 per anhydrous glucose unit ($C_6H_{10}O_5$) and an aqueous solution of water-soluble cellulose ether; and then drying the cast mixture. A hydrous gel sheet having excellent skin adhesion can be prepared only by wetting the film preparation when it is used, leading to the completion of the invention.

In one aspect of the present invention, there are thus provided a film preparation comprising a drug, wetly shear-triturated low-substituted cellulose ether having a molar substitution of 0.05 to 1.0 per anhydrous glucose unit and water-soluble cellulose ether and being capable of adhering to the skin for 100 minutes or greater; and a skin-adhesive hydrous sheet obtained by wetting said film preparation.

In another aspect of the present invention, there is also provided a preparation method of a film preparation, which comprises casting a mixture onto a supporting plate wherein the mixture comprises a drug, wetly shear-triturated low-substituted cellulose ether having a molar substitution of from 0.05 to 1.0 per anhydrous glucose unit and an aqueous solution of water-soluble cellulose ether; and then drying the cast mixture.

According to the present invention, a film preparation containing a desired amount of a drug is excellent in water retention. When the preparation is wetted with water, it has excellent sheet strength and elasticity. It is excellent in skin adhesion and feeling upon use. A skin adhesive hydrous sheet containing an oily substance can also be obtained according to the invention.

DETAILED DESCRIPTION OF THE PREFERRED EMBODIMENTS

The present invention will hereinafter be described in details.

Low-substituted cellulose ether to be used in the present invention is insoluble in water but soluble in an alkaline solution. Cellulose is generally insoluble in water. However, when the hydrogen atom of the hydroxyl group on the glucose ring of the cellulose is substituted with an alkyl or hydroxyalkyl group, the cellulose becomes water-soluble, though depending on the degree of its substitution. When the substitution degree is low, the cellulose is not water-soluble and instead, tends to become soluble in an alkaline solution. In many cases, when low-substituted cellulose ether powder is dispersed in water, it becomes partially swelled with water. When it has a high molar substitution, it becomes water-soluble and loses alkaline solubility.

Low-substituted cellulose ether to be used in the present invention, which is insoluble in water but soluble in an alkali, preferably has a molar substitution of from 0.05 to 1.0. Examples of various low-substituted cellulose ethers (the number in parentheses means a molar substitution degree) may include low-substituted methyl cellulose having 3 to 15 wt % of a methoxyl group (from 0.16 to 0.85), low-substituted hydroxyethyl cellulose having 3 to 15 wt % of a hydroxyethoxyl group (from 0.08 to 0.45), low-substituted hydroxypropyl cellulose having 4 to 20 wt % of a hydroxypropoxyl group (from 0.09 to 0.51) and low-substituted hydroxypropyl methyl cellulose having 3 to 12 wt % of a methoxyl group and 4 to 20 wt % of a hydroxypropoxyl group (from 0.25 to 1.0 in total of both substituents). The substitution degree of a cellulose ether can be measured in accordance with the Japanese Pharmacopoeia.

Such low-substituted cellulose ether is insoluble in water but soluble in an aqueous alkaline solution. It absorbs water and swells. The typical example thereof may include low-substituted hydroxypropyl cellulose, which is commercially available now from Shin-Etsu Chemical Co., Ltd., under the trade name of "L-HPC". It is listed in the Japanese Pharmacopoeia and popularly used as a disintegrant to be incorporated in tablets, particularly in the field of pharmaceutical materials.

A preparation process of such low-substituted cellulose ether is known. For example, as described in Japanese Patent Application Unexamined Publication No. 57-53100/1982, alkali cellulose has to be prepared first. It may be obtained by immersing a starting pulp sheet in an aqueous alkaline solution such as sodium hydroxide; or mixing pulverized pulp directly with an alkaline solution; or adding an alkali to a pulp powder dispersed in an organic solvent. The alkali cellulose thus obtained is placed in a reactor, followed by the addition of an etherifying agent such as propylene oxide or ethylene oxide. The reaction mixture is then heated for the reaction to produce the cellulose ether. After completion of the reaction, the resulting crude cellulose ether is transferred into another tank, where the alkali is neutralized with an acid. The solid thus obtained is washed, dried and then pulverized to produce a powder as a final product. Alternatively, the final product may be prepared by completely or partially dissolving in water the crude cellulose ether just after the reaction, neutralizing the resulting solution, collecting the precipitated polymer, and washing, drying and pulverizing the polymer.

According to the method for producing a film preparation, the film preparation is produced by casting a mixture onto a supporting plate wherein the mixture comprises a drug, wetly shear-triturated low-substituted cellulose ether having a molar substitution of 0.05 to 1.0 per anhydrous glucose unit, and an aqueous solution of water-soluble cellulose ether; and drying the cast mixture. The wetly shear-triturated low-substituted cellulose ether can be obtained by shear-triturating an aqueous dispersion of low-substituted cellulose ether with a wet-type pulverizer.

The aqueous dispersion of low-substituted cellulose ether can be prepared without any special agitator simply by placing the low-substituted cellulose ether in water, or by adding water to the low-substituted cellulose ether for absorption and expansion. The low-substituted cellulose ether can be shear-triturated directly by placing the low-substituted cellulose ether and water in a wet-type pulverizer.

Examples of the wet-type pulverizer may include a vibratory ball mill, a colloid mill, a homomixer, a propeller-type homogenizer, a high-pressure homogenizer, a ultrasonic homogenizer and a wet-type pulverizer of stone-mortar form. The high-pressure homogenizer (e.g. "Ultimaizer", product of Sugino Machine Limited; "Nano-mizer", product of Yoshida Kikai Co., Ltd.; "Microfluidizer", product of Mizuho Industrial Co., Ltd.) are advantageous for obtaining a uniformly shear-triturated product. The pressure for the treatment may be variable depending on a substance to be treated. The pressure may be preferably from 100 to 250 MPa. When the pressure is less than 100 MPa, the satisfactory aqueous dispersion may not be obtained. When the pressure is more than 250 MPa, it may not be suited from the mechanical viewpoint.

According to Japanese Patent Application Unexamined Publication No. 2002-204951, there is a method for obtaining a uniformly shear-triturated product from an aqueous dispersion of low-substituted cellulose ether, the method comprising a step of adding an acid to an alkaline solution of low-substituted cellulose ether for neutralization and precipitation, while mixing the solution with a high speed stirrer. There is also a modified method comprising steps of adding an acid to an alkaline solution of low-substituted cellulose ether to form a gel product as a result of neutralization and precipitation, washing the gel product with hot water and then carrying out wet shear-trituration.

As the preparation of the alkaline solution of low-substituted hydroxyipropyl cellulose, a low-substituted cellulose ether powder as a final product may be dissolved in an aqueous alkaline solution. This method can bring the same result as the method for dissolving in water an alkali-containing crude cellulose ether just after the reaction. In the latter case, the crude cellulose ether contains an alkali so that only water may be added, but an alkali may be added so as to ensure complete dissolution. Both methods are applicable to the present invention.

Examples of the alkali for dissolving the cellulose ether may include potassium hydroxide and sodium hydroxide. The concentration of alkali may vary depending on the kind or substitution degree of the substituent for the cellulose ether so that it may be determined accordingly. The alkali concentration may be preferably 2 to 25 wt %, particularly preferably 5 to 12 wt %. As a typical example, an aqueous 10 wt % sodium hydroxide solution can be used for low-substituted hydroxypropyl cellulose having a molar substitution of 0.2. The solution having the low-substituted hydroxypropyl cellulose dissolved may be transparent or may not be completely transparent, depending on the difference in the substituent distribution for the hydroxypropyl cellulose. Even if the solution is not completely transparent, it is regarded as a solution when the viscosity shows an apparent rise.

Examples of the acid used for neutralization may include organic acid such as acetic acid, formic acid and propionic acid; and inorganic acid such as hydrochloric acid and sulfuric acid. The acid concentration can be selected freely. The preferable acid concentration may be about 5 to 10 wt %.

The concentration of low-substituted cellulose ether which will be subjected to shear-trituration may be preferably from 2 to 20 wt %. When the concentration is less than 2 wt %, the burden for drying may become high. The shear-trituration treatment makes the slurry in the form of gel or sol thicken so that the concentration exceeding 20 wt % may disturb the treatment.

The average particle size of the shear-triturated low-substituted cellulose ether being in the swelling state containing water may be preferably 20 μm or less on basis of the volume as measured by the laser diffraction scattering method. It is known that the particle size of water-insoluble polymer in water has an influence on the film forming property after drying. This also applies to the shear-triturated low-substituted cellulose ether. As the particle size of the shear-triturated low-substituted cellulose ether is smaller, the particles will be packed most closely when the aqueous dispersion thereof is dried. The adjacent particles will coalesce each other, facilitating the formation of a transparent continuous film. The resulting continuous transparent film has high strength in a dry state, and becomes a gel sheet by absorbing water while maintaining its shape. Thus, a skin adhesive hydrous sheet can be obtained. On the other hand, when the average particle size exceeds 20 μm, only a partially-transparent discontinuous film or a sediment of powder can be obtained by drying the aqueous dispersion. The sediment of powder has low strength in the dry state and cannot keep its shape when wetted with water, thus making it impossible to prepare an intended skin-adhesive hydrous sheet. Although no particular limitation is imposed on the lower limit of the particle size, it may be preferably about 1 μm.

Examples of the water-soluble cellulose ether (the numeral in parentheses means a molar substitution) may include alkyl cellulose such as methyl cellulose (a methoxyl group: 1.5 to 2.0), hydroxyalkyl celluloses such as hydroxyethyl cellulose (a hydroxyethyl group: 1.0 to 3.0) and hydroxypropyl cellulose (a hydroxypropyl group: 2.0 to 3.0), hydroxyalkylalkyl celluloses such as hydroxypropylmethyl cellulose (a methoxyl group: 1.1 to 2.0, hydroxypropyl group: 0.1 to 0.4), hydroxyethylmethyl cellulose (a methoxyl group: 1.1 to 2.0, a hydroxyethyl group: 0.1 to 0.4), and carboxymethyl cellulose (carboxymethyl group: 0.5 to 2.5). Hydroxypropylmethyl cellulose may be suited for producing a film preparation containing an oily substance because it has low surface tension and high surface activity and can form a uniform emulsion containing small droplets of oily substance.

The viscosity of the 2 wt % aqueous solution of water-soluble cellulose ether at 20° C. may be preferably from 3 to 4000 mPa·s, especially preferably from 3 to 100 mPa·s. When the viscosity is less than 3 mPa·s, the strength of the obtained film or adhesion to the skin thereof may lower. When the viscosity is more than 4000 mPa·s, the formation of a high concentration solution is difficult so that drying time may prolong or defoaming of the solution may become difficult.

A preparation method for producing the water-soluble cellulose ether is described, for example, in Japanese Patent Application Unexamined Publication No. 10-158302/1998. Alkali cellulose has to be produced first. The alkali cellulose may be produced by immersing a starting pulp sheet, in an aqueous alkaline solution such as sodium hydroxide; or by mixing the pulverized pulp directly with an alkaline solution; or adding an alkali to a pulp powder dispersed in an organic solvent. The alkali cellulose thus obtained may be placed in a reactor, followed by the addition of an etherifying agent such as propylene oxide or ethylene oxide. The mixture may heated for the reaction so that cellulose ether is produced. After completion of the reaction, the resulting crude cellulose ether is transferred into another tank. When the cellulose ether is sparingly soluble in hot water such as methyl cellulose, it is subjected to necessary neutralization and washing with hot water. When the cellulose ether is soluble in both hot water and cool water such as carboxymethyl cellulose, it is subjected to necessary neutralization, followed by washing with a poor solvent such as methanol-containing water. Then, is dried and pulverized to obtain a final power product.

According to the method for producing a film preparation of the present invention, water-soluble cellulose ether may be preferably mixed with an aqueous solution of water-soluble shear-triturated low-substituted cellulose ether and a drug. The concentration of the water-soluble cellulose ether in an aqueous solution can be selected in consideration of the mixing ratio of the low-substituted cellulose ether to water-soluble cellulose ether, or concentration for the casting.

The weight ratio of the low-substituted cellulose ether to the water-soluble cellulose ether for the film preparation of the invention may be preferably from 98/2 to 40/60, more preferably from 95/5 to 50/50. When the ratio is more than 98/2, the film adhered to the skin may peel off before the drug such as a moisturizing agent, an anti-wrinkle agent, an anti-spot agent or a whitening cosmetic starts its action (where the action starts in about 20 minutes). It may be impossible to keep the adhesion for 60 minutes or greater which is at least necessary for the drug to act on the skin. A film containing an oily substance may be prepared by mixing the water-soluble cellulose ether and the oily substance to form an emulsion, and forming the emulsion into the film which supports them uniformly. When the ratio of the low-substituted cellulose ether to water-soluble cellulose ether is larger than 98/2, it may not bring about a sufficient effect and a stable emulsion may not be prepared easily. In this case, the film thus obtained may be uneven.

When the ratio of the low-substituted cellulose ether to the water-soluble cellulose ether is less than 40/60, the film strength after wetting may become weak. After peeling, a portion of the film may remain on the skin so that discomfort may be generated for use of the hydrous sheet.

Although no particular limitation is imposed on the drug to be used in the invention, the present invention is especially effective for the use of an oily substance immiscible with water.

Examples of the drug to be used in the invention may include an anti-wrinkle agent such as retinol; an anti-spot agent such as cysteine; a whitening cosmetics; a moisturizing ingredient such as glycerin, hyaluronic acid, collagen, squalene, docosahexaenoic acid, eicosapentaenoic acid, saccharides, amino acid, placenta extract, sorbitol and polyethylene glycol; a softener such as olive oil, cetyl alcohol, lanolin and stearyl alcohol; a blood circulation promoter such as tocopherol, an anti-inflammatory such as glycyrrhizinic acid; and a skin beautifying agent such as various Vitamin Cs. A pharmaceutical sheet comprising at least one of these ingredients is preferred. If necessary, a water-soluble organic solvent such as alcohol may be added. In use for a percutaneous absorption preparation, examples of the local anesthetic may include tetracaine, diethylaminoethyl parabutylaminobenzoate, oxybuprocaine, lidocaine, dibucaine and propitocaine. Examples of the analgesic antiphlogistic may include aspirin, acetaminophen, ethenzamide, ibuprofen, indomethacin, ketoprofen, glycyrrhizinic acid, flufenamic acid, phenylbutazone, naproxen, oxyphenbutazone, dicrofenac sodium, benzidamine, mepirizole, isothipendyl hydrochloride, bufexamac, bendazac, azulene, piroxicam and diflunisal. Examples of the anti-inflammatory steroid may include triamcinolone acetonide, dexametazone, hydrocortisone acetate, fluocinolone acetonide, prednisolone and betamethasone valerate. Examples of the antibiotic may include penicillin, gentamicin, cefalexin, erythromycin, chloramphenicol and tetracycline. Of these, an oily substance which is liquid at ordinary temperature and is immiscible with water may especially preferable, including retinol, squalane, docosahexaenoic acid, eicosapentaenoic acid, olive oil and tocopherol.

Although the content of the drug is variable depending on its kind, 50 wt % or less in the film preparation may be preferable. When the content is more than 50 wt %, the sheet strength after wetting may lower so that the sheet may remain on the skin as it is peeled off the skin. The conventionally used hydrous sheet which comprises acrylic polymer or agar can hold only several wt % of an oily substance. However, the film of the present invention can advantageously hold about 30 to 40 wt % of the oily substance. It presumably owes to that the low-substituted cellulose ether can retain not only water but also an oily substance and is highly effective for suppressing bleeding.

The film preparation of the invention can be produced by casting a mixture onto a supporting plate wherein the mixture comprises a drug, wetly shear-triturated low-substituted cellulose ether and an aqueous solution of water-soluble cellulose ether and then drying the cast mixture.

The concentration of the mixture to be used for casting is not particularly limited and can be controlled depending on the application purpose. The concentration of the mixture as solid concentration may be, for example, from 2 to 30 wt %.

The casting method of the mixture is not particularly limited and a conventional method can be employed. The material of the supporting plate is not particularly limited and may include glass and Teflon (trade mark). For example, the mixture is cast onto a glass plate with a casting blade to give a proper thickness. The thickness is not particularly limited and can be adjusted depending on the application purpose. The thickness may be preferably between 0.1 mm and 10 mm.

The temperature for drying the film is not particularly limited and may be preferably from 60 to 80° C. The film may be dried preferably until the water content therein becomes about 10 wt % or less. When the drying is insufficient, film formation may be incomplete so that the sheet strength after wetting may lower. The removal of water in the film can improve storage stability of the drug susceptible to water.

The dried film preparation can be used as a sheet having a high water content after wetted with water upon use. The amount of water added for wetting may be selected depending on the application purpose. The film which has absorbed water completely may be preferable. According to the present invention, the water content of the film may be preferably 90 wt % after absorption of water.

As the skin adhesion test, the film is punched out to obtain circular film having a diameter of 2.5 cm as a sample for evaluation. A small amount of water is applied to the circular film to allow it to absorb water therein. The film is applied to the back of the hand and time until the hydrous sheet naturally peels off the hand is measured.

The adhesion time of the sheet to the skin is 100 minutes or greater. Although no upper limit is imposed, it is presumed to be about 400 minutes.

The drug such as a moisturizing agent, an anti-wrinkle agent, an anti-spot agent or a whitening cosmetic with which the sheet is immersed may start its action in about 20 minutes. The minimum time required for the drug to bring its effect may be 60 minutes or greater. The time required for the drug to bring its effect to the full extent may is 100 minutes or greater. The drug such as a moisturizing agent, an anti-wrinkle agent, an anti-spot agent or a whitening cosmetic may not bring its effect when the adhesion time is not greater than 60 minutes, and may not bring its effect completely when the time is not greater than 100 minutes.

The present invention will hereinafter be described by Examples. However, it should not be construed that the present invention is limited to or by these Examples.

EXAMPLE 1

<Preparation of Wetly Shear-Triturated Low-Substituted Cellulose Ether>

A twin-shaft kneader having an internal volume of 5 L was filled with 2360 g of pure water of 25° C. In the kneader, 150 g of low-substituted hydroxypropyl cellulose powder (product of Shin-Etsu Chemical Co., Ltd., molar substitution degree of 0.25) was added and dispersed uniformly. A 49 wt % aqueous NaOH solution (490 g) of 25° C. was added thereto so as to obtain an aqueous NaOH solution of the low-substituted hydroxypropyl cellulose (concentration of the low-substituted hydroxypropyl cellulose: 5 wt %; NaOH concentration: 8 wt %).

The resulting solution was neutralized with 378 g of glacial acetic acid so that a gel-like precipitate was obtained. Hot water was added in an amount of 20 times the weight of the low-substituted hydroxypropyl cellulose to form slurry. The slurry was dehydrated by a centrifugal dehydrator. This operation was repeated again to obtain a washed product of low-substituted hydroxypropyl cellulose.

Pure water was added to the resulting washed product so that a solid concentration reaches 4 wt %, whereby a raw material for wet shear-trituration was obtained. The raw material was wetly shear-triturated with a pulverizer of stone-mortar type ("Cerendipitor MKCA6-31NV", product of Masuko Sangyo Co., Ltd.) under the following conditions:

clearance between the upper and lower grinders: 60 micron, rotation speed: 1500 rpm (peripheral speed: 11.7 m/sec) and treating speed: 1.0 kg/min.

This operation was repeated 5 times to yield wetly shear-triturated low-substituted hydroxypropyl cellulose. The slurry was thickened and became creamy. The measurement of an average particle size with a laser scattering particle size distribution analyzer "HORIBA LA-90" (product of Horiba, Ltd.) showed an average particle size of 10 µm.

<Preparation of Film>

The 87.5 g (solid content: 3.5 g) of 4 wt % slurry containing the wetly shear-triturated low-substituted hydroxypropyl cellulose and 15 g (solid content: 1.5 g) of a 10 wt % aqueous solution of hydroxypropylmethyl cellulose (product of Shin-Etsu Chemical Co., Ltd.; molar substitution degree of the methoxyl group: 1.87; that of the hydroxyproxyl group: 0.23; the viscosity of a 2 wt % aqueous solution at 20° C.: 6 mPa·s) were mixed with stirring at 300 rpm. To the resulting mixture, 1.07 g of α-tocopherol and 1.07 g of ascorbic acid were added and then mixed with stirring at 300 rpm, whereby a uniform creamy emulsion was obtained.

The emulsion was cast onto a glass plate so as to form a film having a thickness of 1.5 mm. The film was dried in a blast oven at 60° C., whereby a transparent continuous film having a thickness of 70 µm and the below-described composition was obtained.

Low-substituted cellulose ether/water-soluble cellulose ether: 7/3 (weight ratio)

Low-substituted hydroxypropyl cellulose: 46.4 wt %
Hydroxypropylmethyl cellulose: 19.9 wt %
α-Tocopherol: 14.2 wt %
Ascorbic acid: 14.2 wt %
Water: 5.3 wt %

The film was punched out into a circular film of 2.5 cm in diameter and was used as a sample for evaluation.

A hydrous sheet obtained by applying a small amount of water to the circular film and allowing it to absorb water therein was attached to the back of the hand. The period of time until the peeling of the film starts, feeling upon use, and the state after the film was peeled off were tested and results are shown in Table 1.

EXAMPLE 2

The 75.0 g (solid content: 3.0 g) of 4 wt % slurry containing the wetly shear-triturated low-substituted hydroxypropyl cellulose which had been prepared in the same manner as in Example 1 and 20.0 g (solid content: 2.0 g) of a 10 wt % aqueous solution of hydroxypropyl cellulose (product of Shin-Etsu Chemical Co., Ltd.; molar substitution degree of the hydroxypropoxyl group: 2.5; the viscosity of a 2 wt % aqueous solution at 20° C.: 6 mPa·s) were mixed with stirring at 300 rpm. To the resulting mixture, 1.07 g of α-tocopherol and 1.07 g of ascorbic acid were added and then mixed with stirring at 300 rpm, whereby a uniform creamy emulsion was obtained.

The emulsion was cast onto a glass plate so as to form a film having a thickness of 1.0 mm. The film was dried in a blast oven at 60° C., whereby a transparent continuous film having a thickness of 60 µm and the below-described composition was obtained.

Low-substituted cellulose ether/water-soluble cellulose ether: 6/4 (weight ratio)

Low-substituted hydroxypropyl cellulose: 40.0 wt %
Hydroxypropyl cellulose: 26.6 wt %
α-Tocopherol: 14.2 wt %
Ascorbic acid: 14.2 wt %
Water: 5.0 wt %

The film was punched out into a circular film of 2.5 cm in diameter and was used as a sample for evaluation.

A hydrous sheet obtained by applying a small amount of water to the circular film and allowing it to absorb water therein was attached to the back of the hand. The period of time until the peeling of the film starts, feeling upon use, and the state after the film was peeled off were tested and results are shown in Table 1.

EXAMPLE 3

Preparation of Wetly Shear-Triturated Low-Substituted Cellulose Ether

In the same manner as in Example 1 except that the low-substituted hydroxypropyl cellulose of Example 1 was replaced with a low-substituted methyl cellulose (molar substitution degree of a methoxyl group: 0.28), a wetly shear-titrated low-substituted cellulose ether was obtained. The resulting slurry was thickened and became creamy. The measurement with laser scattering particle size distribution analyzer "HORIBA LA-90" (product of Horiba, Ltd.) showed an average particle size of 16 µm.

<Preparation of Film>

The 87.5 g (solid content: 3.5 g) of 4 wt % slurry containing the wetly shear-titrated the low-substituted methyl cellulose and 15 g (solid content: 1.5 g) of a 10 wt % aqueous solution of hydroxypropylmethyl cellulose (product of Shin-Etsu Chemical Co., Ltd.; molar substitution of the methoxyl group: 1.3; that of the hydroxypropoxyl group: 0.21, the viscosity of a 2 wt % aqueous solution at 20° C.: 100 mPa·s) were mixed. To the resulting mixture, 1.5 g of α-tocopherol and 0.64 g of ascorbic acid were added and then mixed with stirring at 300 rpm, whereby a uniform creamy emulsion was obtained.

The resulting emulsion was cast onto a glass plate to form a film having a thickness of 1.5 mm. The film was dried in a blast oven at 60° C., whereby a transparent continuous film having a thickness of 70 µm and the below-described composition was obtained.

Low-substituted cellulose ether/water-soluble cellulose ether: 7/3 (weight ratio)

Low-substituted methyl cellulose: 46.4 wt %
Hydroxypropylmethyl cellulose: 19.9 wt %
α-Tocopherol: 20.0 wt %
Ascorbic acid: 8.6 wt %
Water: 5.1 wt %

The film was punched out into a circular film of 2.5 cm in diameter and was used as a sample for evaluation.

A hydrous sheet obtained by applying a small amount of water to the circular film and allowing it to absorb water therein was attached to the back of the hand. The period of time until the peeling of the film starts, feeling upon use, and the state after the film was peeling were tested and results are shown in Table 1.

EXAMPLE 4

Preparation of Wetly Shear-Triturated Low-Substituted Cellulose Ether

In a same manner as in Example 1 except that the low-substituted hydroxypropyl cellulose used in Example 1 was replaced with low-substituted hydroxypropylmethyl cellulose (product of Shin-Etsu Chemical CO., Ltd.; molar substitution degree of a methoxyl group: 0.13; that of a hydroxypropoxyl group: 0.18), wetly shear-triturated low-substituted cellulose ether was obtained. The slurry was thickened and became creamy. The measurement with a laser scattering particle size distribution analyzer "HORIBA LA-90" (product of Horiba, Ltd.) showed an average particle size of 16 μm.

<Preparation of Film>

The 112.5 g (solid content: 4.5 g) of 4 wt % slurry containing the wetly shear-triturated low-substituted hydroxypropylmethyl cellulose and 2.5 g (solid content: 0.25 g) of a 10 wt % aqueous solution of hydroxypropylmethyl cellulose (product of Shin-Etsu Chemical Co., Ltd.; molar substitution degree of a methoxyl group: 1.8; that of a hydroxyproxyl group: 0.16; the viscosity of a 2 wt % aqueous solution at 20° C.: 5 mPa·s) were mixed. To the resulting mixture, 1.07 g of α-tocopherol and 1.07 g of glycerin were added and then were mixed with stirring at 300 rpm, whereby a uniform creamy emulsion was obtained.

The emulsion was cast onto a glass plate so as to form a film having a thickness of 1.5 mm. The film was dried in a blast oven at 60° C., whereby a transparent continuous film having a thickness of 70 μm and the below-described composition was obtained.

Low-substituted cellulose ether/water-soluble cellulose ether: 9/1 (weight ratio)

Low-substituted hydroxypropylmethyl cellulose: 60.0 wt %

Hydroxypropylmethyl cellulose: 6.6 wt %

α-Tocopherol: 14.2 wt %

Glycerin: 14.2 wt %

Water: 5.0 wt %

The film was punched out into a circular film of 2.5 cm in diameter and was used as a sample for evaluation.

A hydrous sheet obtained by applying a small amount of water to the circular film and allowing it to absorb water therein was attached to the back of the hand. The period of time until the peeling of the film starts, feeling upon use, and the state after the film was peeled off were tested and results are shown in Table 1.

COMPARATIVE EXAMPLE 1

A 10 wt % aqueous dispersion of the low-substituted hydroxypropyl cellulose powder (product of Shin-Etsu Chemical Co., Ltd.; molar substitution of 0.25) which was employed as a raw material for the wetly shear-triturated product in Example 1 was prepared. The measurement of an average particle size with a laser scattering particle size distribution analyzer "HORIBA LA-90" (product of Horiba, Ltd.) showed 150 μm. The 35.0 g (solid content: 3.5 g) of the resulting dispersion and 15 g (solid content: 1.5 g) of a 10 wt % aqueous solution of hydroxypropylmethyl cellulose (product of Shin-Etsu Chemical Co., Ltd.; molar substitution degree of a methoxyl group: 1.87; that of a hydroxypropoxyl group: 0.23; viscosity of a 2 wt % aqueous solution at 20° C.: 6 mPa·s) were mixed with stirring at 300 rpm. To the resulting mixture, 1.07 g of α-tocopherol and 1.07 g of ascorbic acid were added and then mixed with stirring at 300 rpm.

The resulting dispersion was cast onto a glass plate so as to form a film having a thickness of 1.0 mm. The film was dried in a blast oven at 60° C., whereby a film having transparency in some parts and white discontinuous powder deposits in some parts was obtained. The film strength was low. When the film was wetted with a small amount of water, it lost its shape so that it could not be subjected to the test for adhesion to the skin.

COMPARATIVE EXAMPLE 2

The low-substituted hydroxypropyl cellulose powder (product of Shin-Etsu Chemical Co., Ltd.; molar substitution degree of 0.25) used as a raw material for the wetly shear-triturated product in Example 1 was finely pulverized with a dry jet mill to prepare a 10 wt % aqueous dispersion thereof. The measurement of an average particle size of the aqueous dispersion with a laser scattering particle size distribution analyzer "HORIBA LA-90" (product of Horiba, Ltd.) showed 60 μm. The 35.0 g (solid content: 3.5 g) of the resulting aqueous dispersion and 15 g (solid content: 1.5 g) of a 10 wt % aqueous solution of "Hydroxypropylmethyl cellulose 2910" (product of Shin-Etsu Chemical Co., Ltd.; molar substitution degree of a methoxyl group: 1.87; that of a hydroxypropoxyl group: 0.23; viscosity of a 2 wt % aqueous solution at 20° C.: 6 mPa·s) were mixed with stirring at 300 rpm. To the resulting mixture, 1.07 g of α-tocopherol and 1.07 g of ascorbic acid were added and mixed with stirring at 300 rpm.

The resulting dispersion was cast onto a glass plate so as to form a film having a thickness of 1.0 mm. The film was dried with a blast oven at 60° C., whereby a film having transparency in some parts and white discontinuous powder deposits in some parts was obtained. The film strength was low. When the film was wetted with a small amount of water, it lost its shape so that it could not be subjected to the test for adhesion to the skin.

COMPARATIVE EXAMPLE 3

The low-substituted hydroxypropyl cellulose powder (product of Shin-Etsu Chemical Co., Ltd.; molar substitution degree of 0.25) which was a raw material for the wetly shear-triturated product in Example 1 was finely pulverized with a dry jet mill. A 7 wt % aqueous dispersion of the resulting fine powder was wetly shear-triturated with a pulverizer of stone-mortar type ("Cerendipitor MKCA6-31NV", product of Masuko Sangyo Co., Ltd.) under the following conditions:

clearance between the upper and lower grinders: 80 micron, rotation speed: 1500 rpm (peripheral speed: 11.7 m/sec), and treating velocity; 1.5 kg/min.

This operation was repeated 5 times to yield wetly shear-triturated low-substituted hydroxypropyl cellulose.

The slurry thus obtained was thickened slightly. The measurement of an average particle size with a laser scattering particle size distribution analyzer "HORIBA LA-90" (product of Horiba, Ltd.) showed 40 μm.

The 50.0 g (solid content: 3.5 g) of the aqueous dispersion and 15 g (solid content: 1.5 g) of a 10 wt % aqueous solution of hydroxypropylmethyl cellulose (product of Shin-Etsu Chemical Co., Ltd.; molar substitution degree of the methoxyl group: 1.87; that of the hydroxypropoxyl group: 0.23; the viscosity of a 2 wt % aqueous solution at 20° C.: 6 mPa·s) were mixed with stirring at 300 rpm. To the resulting mixture, 1.07 g of α-tocopherol and 1.07 g of ascorbic acid were added and mixed with stirring at 300 rpm.

The resulting dispersion was cast onto a glass plate so as to form a film having a thickness of 1.0 mm. The film was dried with a blast oven at 60° C., whereby a film having transparency in some parts and white discontinuous powder deposits in some parts was obtained. The film strength was low. When the film was wetted with a small amount of water, it lost its shape so that it could not be subjected to the test for adhesion to the skin.

COMPARATIVE EXAMPLE 4

To 125.0 g (solid content: 5.0 g) of the 4 wt % slurry of the wetly shear-triturated low-substituted hydroxypropyl cellulose prepared in the same manner as in Example 1, 1.07 g of glycerin and 1.07 g of ascorbic acid were added and mixed with stirring at 300 rpm to yield a uniform creamy emulsion. The emulsion was cast onto a glass plate so as to form a film having a thickness of 1.5 mm thickness. The film was dried with a blast oven at 60° C., whereby a transparent continuous film having a thickness of 50 μm and the below-described composition was obtained.

Low-substituted hydroxypropyl cellulose: 66.4 wt %
Glycerin: 14.2 wt %
Ascorbic acid: 14.2 wt %
Water: 5.2 wt %

The resulting film was punched out into a circular film having a diameter of 2.5 cm and used as a sample for evaluation.

A hydrous sheet obtained by applying a small amount of water to the circular film and allowing it to absorb water therein was attached to the back of the hand. The period of time until the peeling of the film starts, feeling upon use, and the state after peeling were tested and results are shown in Table 1.

TABLE 1

|  | Adhesion time to the skin (minute) | Flexibility | Adhesion | Skin state after peeling of film |
|---|---|---|---|---|
| Example 1 | 160 | A | A | A |
| Example 2 | 240 | A | A | A |
| Example 3 | 150 | A | A | A |
| Example 4 | 105 | A | A | A |
| Comp. Ex. 1 | Film lost its shape when wetted with a small amount of water | | | |
| Comp. Ex. 2 | Film lost its shape when wetted with a small amount of water | | | |
| Comp. Ex. 3 | Film lost its shape when wetted with a small amount of water | | | |
| Comp. Ex. 4 | 20 | B | C | B |

In Table 1, "flexibility" is evaluated based on the following criteria:
A: flexible and elastic,
B: flexible but less elastic, and
C: not flexible.

"Adhesion" is evaluated based on the following criteria:
A: good adhesion to the skin,
B: not so good adhesion to the skin, and
C: poor adhesion to the skin.

"Skin state after peeling" is evaluated based on the following criteria:
A: moist and smooth,
B: slightly moisturized feeling, and
C: no improvement.

The results shown in Table 1 proved that the hydrous sheets obtained in Examples were excellent in skin adhesion and feeling upon use.

What is claimed is:

1. A method for producing a film preparation, the method comprising a step of casting a mixture onto a supporting plate wherein the mixture comprises a drug, wetly shear-triturated low-substituted cellulose ether having a molar substitution of from 0.05 to 1.0 per anhydrous glucose unit and an average particle size of 20 μm or less in the swelling state by containing water, and an aqueous solution of water-soluble cellulose ether, and the weight ratio of the low-substituted cellulose ether to the water-soluble cellulose ether is from 98:2 to 40:60; and a step of drying the cast mixture.

2. The method according to claim 1, wherein the wetly shear-triturated low-substituted cellulose ether has an average particle size from 1 to 20 μm.

3. The method according to claim 1, wherein the weight ratio of the low-substituted cellulose ether to the water-soluble cellulose ether is from 95:5 to 50:50.

4. The method according to claim 1, wherein the drug comprises an oily substance that is immiscible with water.

5. The method according to claim 1, wherein casting a mixture onto a supporting plate comprises casting the mixture onto the supporting plate to provide a thickness from between 0.1 mm and 10 mm.

* * * * *